(12) United States Patent
Lucero et al.

(10) Patent No.: US 8,828,661 B2
(45) Date of Patent: Sep. 9, 2014

(54) METHODS FOR DETECTION AND QUANTIFICATION OF NUCLEIC ACID OR PROTEIN TARGETS IN A SAMPLE

(75) Inventors: Michael Lucero, South San Francisco, CA (US); Marc Unger, San Mateo, CA (US)

(73) Assignee: Fluidigm Corporation, South San Francisco, CA (US)

( * ) Notice: Subject to any disclaimer, the term of this patent is extended or adjusted under 35 U.S.C. 154(b) by 1169 days.

(21) Appl. No.: 11/739,660

(22) Filed: Apr. 24, 2007

(65) Prior Publication Data

US 2008/0108063 A1 May 8, 2008

Related U.S. Application Data

(60) Provisional application No. 60/794,812, filed on Apr. 24, 2006.

(51) Int. Cl.
*C12Q 1/68* (2006.01)
*C12P 19/34* (2006.01)

(52) U.S. Cl.
USPC ......................................... 435/6.12; 435/91.2

(58) Field of Classification Search
None
See application file for complete search history.

(56) References Cited

U.S. PATENT DOCUMENTS

| | | | |
|---|---|---|---|
| 5,723,591 A | 3/1998 | Livak et al. |
| 6,540,895 B1 | 4/2003 | Spence et al. |
| D488,818 S | 4/2004 | Lee et al. |
| 6,885,982 B2 | 4/2005 | Harris et al. |
| 6,951,632 B2 | 10/2005 | Unger et al. |
| 7,042,649 B2 | 5/2006 | Quake et al. |
| 7,059,348 B2 | 6/2006 | Nat |
| 7,062,418 B2 | 6/2006 | Lee et al. |
| 7,097,809 B2 | 8/2006 | Dam et al. |
| 7,118,910 B2 | 10/2006 | Unger et al. |
| 7,161,736 B2 | 1/2007 | Legrand et al. |
| 7,192,629 B2 | 3/2007 | Lammertink et al. |
| 7,217,367 B2 | 5/2007 | Huang et al. |
| 7,232,109 B2 | 6/2007 | Driggs et al. |
| 7,248,413 B2 | 7/2007 | Quake et al. |
| 7,262,923 B2 | 8/2007 | Quake et al. |
| 7,279,146 B2 | 10/2007 | Nassef |
| 7,291,512 B2 | 11/2007 | Unger |
| 7,368,163 B2 | 5/2008 | Huang et al. |
| 7,442,556 B2 | 10/2008 | Manger et al. |
| 7,476,363 B2 | 1/2009 | Unger et al. |
| 7,526,741 B2 | 4/2009 | Lee et al. |
| 7,604,965 B2 | 10/2009 | McBride et al. |
| 7,666,361 B2 | 2/2010 | McBride et al. |
| 7,678,547 B2 | 3/2010 | Eyal et al. |
| 7,691,333 B2 | 4/2010 | McBride et al. |
| 7,749,737 B2 | 7/2010 | McBride et al. |
| 7,792,345 B2 | 9/2010 | Taylor et al. |
| 7,815,868 B1 | 10/2010 | Jones et al. |
| 7,820,427 B2 | 10/2010 | Unger et al. |
| 7,833,708 B2 | 11/2010 | Enzelberger et al. |
| 7,837,946 B2 | 11/2010 | McBride et al. |
| 2002/0064779 A1 | 5/2002 | Landegren et al. |
| 2004/0180377 A1 | 9/2004 | Manger et al. |
| 2005/0053952 A1 | 3/2005 | Hong et al. |
| 2005/0252773 A1 | 11/2005 | McBride et al. |
| 2006/0172408 A1 | 8/2006 | Quake et al. |
| 2006/0281183 A1 | 12/2006 | Sun et al. |
| 2007/0065847 A1* | 3/2007 | Namsaraev et al. ............. 435/6 |
| 2007/0134807 A1 | 6/2007 | Bao et al. |
| 2007/0224617 A1 | 9/2007 | Quake et al. |
| 2007/0248971 A1 | 10/2007 | Maerkl et al. |
| 2008/0050283 A1 | 2/2008 | Chou et al. |
| 2008/0075380 A1 | 3/2008 | Dube et al. |
| 2008/0108063 A1 | 5/2008 | Lucero et al. |
| 2008/0129736 A1 | 6/2008 | Sun et al. |
| 2008/0176211 A1 | 7/2008 | Spence et al. |
| 2008/0223721 A1 | 9/2008 | Cohen et al. |
| 2008/0230387 A1 | 9/2008 | McBride et al. |
| 2008/0264863 A1 | 10/2008 | Quake et al. |
| 2008/0274493 A1 | 11/2008 | Quake et al. |
| 2008/0281090 A1 | 11/2008 | Lee et al. |
| 2008/0292504 A1 | 11/2008 | Goodsaid et al. |
| 2009/0018195 A1 | 1/2009 | Balagadde |
| 2009/0035838 A1 | 2/2009 | Quake et al. |
| 2009/0069194 A1 | 3/2009 | Ramakrishnan |
| 2009/0142236 A1 | 6/2009 | Unger et al. |
| 2009/0147918 A1 | 6/2009 | Fowler et al. |
| 2009/0239308 A1 | 9/2009 | Dube et al. |
| 2009/0291435 A1 | 11/2009 | Unger et al. |

(Continued)

FOREIGN PATENT DOCUMENTS

WO    WO 2005107938 A2    11/2005

OTHER PUBLICATIONS

Roth et al., Expression profiling using a hexamer-based universal microarray, vol. 22, No. 4, Apr. 2004, Nature Biotechnology, pp. 418-426.*

Supplemenal Table 3, Roth et al., Expression profiling using a hexamer-based universal microarray, vol. 22, No. 4, Apr. 2004, Nature Biotechnology, two pages.*

(Continued)

*Primary Examiner* — Kenneth R. Horlick
*Assistant Examiner* — David Thomas
(74) *Attorney, Agent, or Firm* — Kilpatrick Townsend & Stockton LLP

(57) ABSTRACT

The invention provides an assay method for detection and/or quantification of a plurality of nucleic acid or protein targets in a sample. In the method probes are used to associate a detectable tag sequence with each of the selected targets present in the sample. Probes or primers sufficient to identify at least 25, and preferably at least 500, different targets are used. The method involves segregating aliquots of the sample from each other and detecting the tag sequences in each aliquot.

18 Claims, 2 Drawing Sheets

(56) References Cited

U.S. PATENT DOCUMENTS

| | | | |
|---|---|---|---|
| 2009/0317798 A1* | 12/2009 | Heid et al. | 435/6 |
| 2010/0120077 A1 | 5/2010 | Daridon | |
| 2010/0154890 A1 | 6/2010 | Maerkl et al. | |
| 2010/0166608 A1 | 7/2010 | Quan et al. | |
| 2010/0171954 A1 | 7/2010 | Quake et al. | |
| 2010/0183481 A1 | 7/2010 | Facer et al. | |
| 2010/0184202 A1 | 7/2010 | McBride et al. | |
| 2010/0187105 A1 | 7/2010 | Unger et al. | |
| 2010/0196892 A1 | 8/2010 | Quake et al. | |
| 2010/0197522 A1 | 8/2010 | Liu et al. | |
| 2010/0200782 A1 | 8/2010 | Unger et al. | |
| 2010/0230613 A1 | 9/2010 | Pieprzyk et al. | |
| 2010/0263732 A1 | 10/2010 | Hansen et al. | |
| 2010/0263757 A1 | 10/2010 | Fernandes et al. | |
| 2010/0311060 A1 | 12/2010 | Facer et al. | |
| 2010/0320364 A1 | 12/2010 | Unger et al. | |

OTHER PUBLICATIONS

Baner et al., Parallel gene analysis with allele-specific padlock probes and tag microarrays, Nucleic Acids Research, 2003, vol. 31, No. 17 e103, pp. 1-7.*

Ng et al., Review, Components for integrated poly(dimethylsiloxane) microfluidic systems, Electrophoresis 2002, 23, pp. 3461-3473.*

Cao, Review, Recent developments in ligase-mediated amplification and detection, TRENDS in Biotechnology, vol. 22, No. 1, Jan. 2004, pp. 38-44.*

Gullberg et al., Cytokine Detection by Antibody-Based Proximity Ligation, *Proc Natl. Acad Sci USA*, 101(22):8420-8440 (2004).

Fredriksson et al., "Protein Detection Using Proximity-Dependent DNA Ligation Assays," *Nat Biotechnol.*, 20:473-477(2002).

Heid et al., "Real Time Quantitative PCR," *Genome Res.*, 6:986-994 (1996).

Landegren et al., Padlock and Proximity Probes for in Situ and Array-Based Analyses: Tools for the Post-genomic Era, *Comparative and Functional Genomics*, 4:525-530 (2003).

Landegren et al., "Molecular Tools for a Molecular Medicine: Analyzing Genes, Transcripts, Proteins Using Padlock and Proximity Probes," *J Mol Recognit.*, 7:194-197 (2004).

Nilsson et al., Analyzing Genes Using Closing and Replicating Circles, *Trends Biotechnol.*, 24:83-88 (2006).

Nilsson et al., Padlock Probes: Circularizing Oligonucleotides for Localizing DNA Detection, *Science*, 265:2085-2088 (1994).

Szemes et al., Diagnostic Application of Padlock Probes—Multiplex Detection of Plant Pathogens Using Universal Microarrays, *Nucleic Acids Res.*, 33(8):e70 (2005).

* cited by examiner

Selectivity can be on the basis of primers as well as probes:

For example, using multiple different tags:

Alternatively, using multiple different primers F and R:

METHODS FOR DETECTION AND QUANTIFICATION OF NUCLEIC ACID OR PROTEIN TARGETS IN A SAMPLE

CROSS REFERENCE TO RELATED APPLICATIONS

This application claims priority to U.S. provisional application No. 60/794,812 (filed Apr. 24, 2006) the entire content of which is incorporated herein by reference.

FIELD OF THE INVENTION

The field of the invention is high-throughput analysis of analytes in a sample using a microfluidic device.

BACKGROUND OF THE INVENTION

The ability to detect specific nucleic acid sequences in a sample has resulted in new approaches in diagnostic and predictive medicine, environmental, food and agricultural monitoring, molecular biology research, and many other fields. High-throughput detection of specified epitopes, proteins, and protein complexes promises to have a similar impact.

Various methods for such analysis have been developed, including multiplexing methods that allow simultaneous detection of large numbers of targets. Additional methods, especially methods that allow detection of many targets across a broad range of concentrations in a sample would be of great benefit.

SUMMARY OF THE INVENTION

In one aspect the invention provides an assay method for detection of a plurality of nucleic acid or protein targets in a sample. In one aspect the method involves (1) combining target-specific probes with the sample under conditions in which the probe binds a target, if the target is present in the sample, and where: (i) target-specific probes sufficient to identify at least 25 different targets are used, (ii) each probe comprises a nucleic acid tag sequence, and (iii) the target-specific probe forms a target-specific probe product associated with the target if the target is present in the sample, thereby associating the tag with the target; (2) distributing aliquots of the sample to separate compartments of a microfluidic device and segregating the aliquots from each other; (3) querying each aliquot of the sample for the presence of a different target-specific probe product, wherein said querying comprises detecting the nucleic acid tag sequence if present in the aliquot. In one embodiment target-specific probes sufficient to identify at least 500 different targets are combined with the sample. In one embodiment the assay has a dynamic range of at least 4 orders of magnitude.

In one embodiment the querying step involves combining each aliquot with a composition containing one or two amplification (e.g., PCR) primers and/or a tag detecting probe. In one embodiment the tag sequence is amplified using PCR. In one embodiment the amplified tag sequence is detected using a fluorogenic nuclease assay. In one embodiment the tag-detecting probe is a dual-labeled fluorogenic oligonucleotide probe. In one embodiment each aliquot is queried using the same tag-detecting probe and a different PCR primer pair. In another embodiment each aliquot is queried using the same PCR primer pair and a different tag-detecting probe.

In one embodiment the querying step includes quantifying the amount of the nucleic acid tag sequence in each aliquot and correlating the amount of the tag sequence with the amount of target in the sample. For example, in one embodiment each nucleic acid tag sequence molecule may correspond to one target-specific probe, and each target specific-probe may correspond to one molecule of target. In one embodiment the amplified tag sequence is quantified by the continuous measurement of PCR product accumulation using a dual-labeled fluorogenic oligonucleotide (TaqMan®) probe.

In one embodiment of the invention the target is a nucleic acid molecule and the target-specific probe is a padlock probe. In another embodiment of the invention the target is a polypeptide (e.g., protein) molecule and the target-specific probe is a proximity probe.

In one embodiment the microfluidic device is fabricated, at least in part, from an elastomeric material. In some embodiments, and without limitation, the aliquot has a volume of from 1 picoliter to 500 nanoliters, more often from 100 picoliters to 20 nanoliters, even more often from 1 nanoliter to 20 nanoliters, and most often from 5 nanoliters to 15 nanoliters.

In one embodiment the invention provides an assay method for detection of a plurality of DNA targets in a sample involving (1) combining target-specific padlock probes sufficient to identify at least 25 different targets with the sample under conditions in which the probes bind and catenate to the target molecules, if present, forming a target-specific probe product, where each probe comprises a nucleic acid tag sequence and the padlock probes form target-specific probe products associated with the target if the target is present in the sample, thereby associating the tag sequence with the target; (2) distributing aliquots of the sample to separate compartments of a microfluidic device and segregating the aliquots from each other; and (3) querying each aliquot for the presence of a different probe molecule catenated to the target, where the querying includes detecting, and optionally quantifying, the tag sequence if present in the aliquot, and where detecting and/or quantifying the tag includes amplifying the tag sequence using PCR primers and detecting the amplification using a dual-labeled fluorogenic oligonucleotide probe. The presence of amount of tag sequence can be correlated with the presence or amount of target in the sample.

BRIEF DESCRIPTION OF THE FIGURES

FIG. 2 illustrates methods of the invention showing that selectivity can be based on either tags or primers. Ellipses indicate circularized padlock probes that would be formed if a target target nucleic acid is present. In this illustration there are 48 potential PLP products that could be detected in each sample, each with different termini and tag sequence (each numbered 1-48).

FIG. 3 illustrates methods of the invention showing an assay of 2304 different targets in a single sample, as illustrated in Example 5. Symbols are as in FIG. 2B. The upper portion of the figure illustrates potential products in a 48×48 array (in this illustration 9 products are shown with others indicated by ellipses).

DETAILED DESCRIPTION OF THE INVENTION

1. Matrix-Type Microfluidic Device

Figure 1:
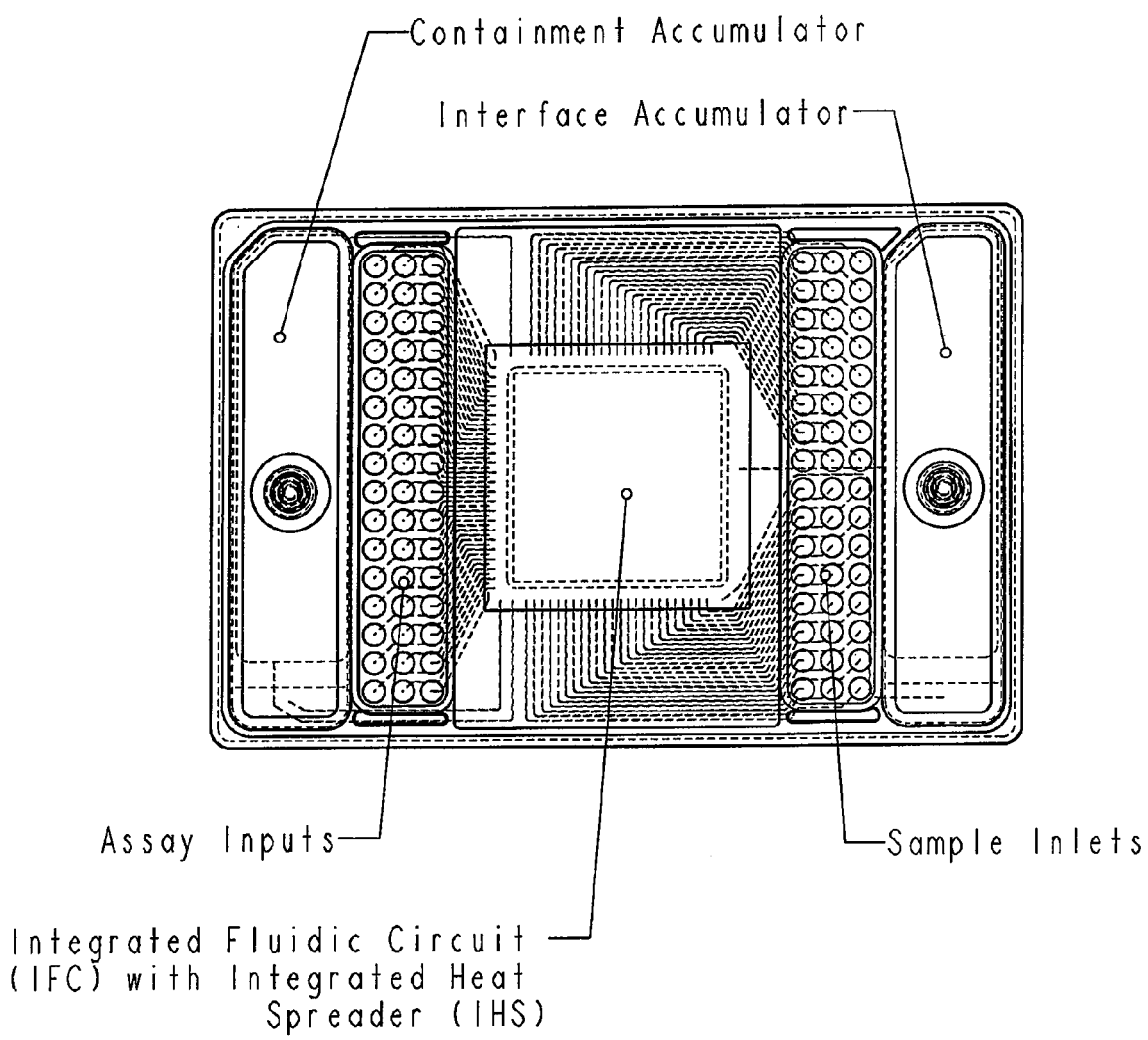
FIG. 1 shows a diagram of the 48.48 Dynamic Array Microfluidic Device (Fluidigm Corp.) with an integrated input frame. The parallel lines leading from the sample and assay wells are channels for routing fluids into the integrated fluid circuit (IFC). The accumulators hold pressure that operates valves, within the IFC, necessary for routing fluids during loading and containing reaction components once the chip has been loaded.

The present method is conducted using a matrix-type microfluidic device. A matrix-type device is one that allows the simultaneous pair-wise combination of a plurality of substrate/reagent pairs in separate isolated reaction chambers, for example, the simultaneous pair-wise combination of a plurality of targets and probes. Preferably the device is configured to contain a different combination of probes and targets in each of the different chambers. The number of separate reaction chambers is greater than 50, usually greater than 100, more often greater than 500, even more often greater than 1000, and sometimes greater than 5000, or greater than 10,000.

In an aspect of the invention, the matrix-type microfluidic device is a Dynamic Array microfluidic device ("DA"). A DA microfluidic device is an matrix-type microfluidic device, designed to isolate pair-wise combinations of targets and reagents (e.g., amplification primers, detection probes, PCR primers, TaqMan® probes, etc.), and suited for carrying out qualitative and quantitative PCR reactions including real-time quantitative PCR analysis. In some embodiments, the DA microfluidic device is fabricated, at least in part, from an elastomer. Dynamic Arrays are described in PCT publication WO05107938A2 (Thermal Reaction Device and Method For Using The Same) and US Pat. Publication US20050252773A1, both incorporated by reference. FIG. 21 of this publication depicts an exemplary matrix design. DAs may incorporate high-density matrix designs that utilize fluid communication vias between layers of the microfluidic device to weave control lines and fluid lines through the device and between layers, as shown in FIG. 21. By having a fluid lines in multiple layers of an elastomeric block, higher density reaction cell arrangements are possible. Alternatively DAs may be designed so that all of the reagent and sample channels are in the same elastomeric layer, with control channels in a different layer.

FIG. 21 of WO05107938A2 depicts an exemplary matrix design having a first elastomeric layer 2110 (1st layer) and a second elastomeric layer 2120 (2d layer) each having fluid channels formed therein. For example, a reagent fluid channel in the first layer 2110 is connected to a reagent fluid channel in the second layer 2120 through a via 2130, while the second layer 2120 also has sample channels therein, the sample channels and the reagent channels terminating in sample and reagent chambers 2180, respectively. The sample and reagent chambers 2180 are in fluid communication with each other through an interface channel 2150 that has an interface valve 2140 associated therewith to control fluid communication between each of the chambers 2180 of a reaction cell 2160. In use, the interface is first closed, then reagent is introduced into the reagent channel from the reagent inlet and sample is introduced into the sample channel through the sample inlet, containment valves 2170 are then closed to isolate each reaction cell 2160 from other reaction cells 2160. Once the reaction cells 2160 are isolated, the interface valve 2140 is opened to cause the sample chamber and the reagent chamber to be in fluid communication with each other so that a desired reaction may take place. It will be apparent from this (and the description in WO05107938A2) that the DA may be used for reacting M number of different samples with N number of different reagents.

Although the Dynamic Array described above in WO05107938 are well suited for conducting the assays of the invention, the invention is not limited to any particular device or design. Any device that partitions a sample, and allows independent pair-wise combinations of reagents and sample may be used. FIG. 1 is a diagram illustrating the 48.48 Dynamic Array, a commercially available device available from Fluidigm Corp. (South San Francisco Calif.). This device is also described infra in Example 6.

In one aspect the invention relates to the use of a partitioning microfluidic device for detection and/or quantification of a plurality of targets in a sample, each target being associated with an amplifiable tag sequence. The number of targets detected is at least 10, more often at least 25, still more often at least 50, even more often at least 100, and in some cases 500 or more.

2. Padlock Probes

Padlock probes (PLPs) are long (e.g., about 100 bases) linear oligonucleotides. The sequences at the 3' and 5' ends of the probe are complementary to adjacent sequences in the target nucleic acid. In the central, noncomplementary region of the PLP there is a "nucleic acid tag" sequence that can be used to identify the specific PLP. The tag sequence is flanked by universal priming sites, which allow PCR amplification of the tag. Upon hybridization to the target, the two ends of the PLP oligonucleotide are brought into close proximity and can be joined by enzymatic ligation. The resulting product is a circular probe molecule catenated to the target DNA strand. Any unligated probes (i.e., probes that did not hybridize to a target) are removed by addition of an exonuclease. Hybridization and ligation of a PLP requires that both end segments recognize the target sequence. In this manner, PLPs provide extremely specific target recognition.

Using universal primers, the tag regions of circularized PLPs can be amplified and resulting amplicons detected. For example, TaqMan® real time PCR can be carried out to detect and quantify the amplicon. The presence and amount of amplicon can be correlated with the presence and quantity of target sequence in the sample. For descriptions of PLPs see, e.g., Landegren et al., 2003, Padlock and proximity probes for in situ and array-based analyses: tools for the post-genomic era, *Comparative and Functional Genomics* 4:525-30; Nilsson et al., 2006, Analyzing genes using closing and replicating circles *Trends Biotechnol.* 24:83-8; Nilsson et al., 1994, Padlock probes: circularizing oligonucleotides for localized DNA detection, *Science* 265:2085-8. Each of the these references is incorporated herein by reference.

In an alternative embodiment, the sequences at the 3' and 5' ends of each padlock probe are complementary to adjacent sequences in the target nucleic acid, there is a common "tag" sequence that can be used to detect PLP products, and the tag sequence for each probe is flanked by a unique pair of priming sites, which allow PCR amplification of the tag. Upon hybridization to the target, the two ends of the PLP oligonucleotide are brought into close proximity and can be joined by enzymatic ligation. The resulting product is a circular probe molecule catenated to the target DNA strand. Any unligated probes (i.e., probes that did not hybridize to a target) are removed by addition of an exonuclease. Specific primers can be used to amplify the tag regions of circularized PLPs, and the resulting amplicons detected.

PLP probes may be multiplexed and a large number of different targets (>1000) can be detected in a single reaction by using an equivalent number of different PLPs. However, quantitative analysis is problematic. TaqMan® and other FRET probe-based assays are not readily multiplexed, in part because multiplex fluorescence detection using many different probes is limited by high fluorescence background when many different probes are used in an assay. For this reason, current approaches to multiplex PLP-based analysis rely on analysis by hybridization of amplicons to microarrays. However, the dynamic range of array analysis is limited. For example, in a highly optimized system in which a relatively few number of targets were probed, investigators reported a dynamic range of only 100-1000. Szemes et al., 2005, Diagnostic application of padlock probes—multiplex detection of plant pathogens using universal microarrays, *Nucleic Acids Res.* 33(8):e70, incorporated herein by reference. In contrast, TaqMan®-based approaches generally have a dynamic range of 5-8 orders of magnitude or more. Dynamic range, as used here, has its usual meaning in the art and refers to the range of concentrations of an analyte that can be accurately measured by an assay. For example, an assay that can accurately measure quantities of 5 nanograms and 5 micrograms has a dynamic range of 1000 or $10^3$. An assay that can accurately measure quantities of 10 picograms and 10 micrograms has a dynamic range of $10^6$.

3. Proximity Ligation for Protein Detection

The proximity ligation procedure is analogous in certain respects to the use of padlock probes, but is used for detecting proteins and other analytes. The proximity ligation procedure uses specific protein binding agents linked to oligonucleotides. Examples of specific protein binding agents include antibodies (defined as any specific binding agent comprising a CDR, including phage display antibodies, single chain antibodies, monoclonal antibodies, and the like) and nucleic acid aptamers. The proximity ligation procedure is described in Landegren et al., 2003, supra; Landegren et al., 2004, Molecular tools for a molecular medicine: analyzing genes, transcripts and proteins using padlock and proximity probes, *J Mol Recognit.* 7:194-7; Gullberg et al., 2004, Cytokine detection by antibody-based proximity ligation, *Proc Natl Acad Sci USA* 101(22):8420-4; Fredriksson et al., 2002, Protein detection using proximity-dependent DNA ligation assays, *Nat Biotechnol.* 20:448-9; and Landegren, 2002, Methods and kits for proximity probing U.S. Patent Application 20020064779. Each of the these references is incorporated herein by reference. Briefly, a pair of protein binding agents that recognize different epitopes of a target protein are used. Each of the binding agents is attached (e.g., via streptavidin-biotin linkage) to a synthetic DNA strand that includes a PCR primer binding site. The synthetic DNA strands are brought into proximity when both binding agents bind the same target molecule. A connector oligonucleotide that hybridizes to sequences at the ends of both of the synthetic DNAs is added in excess, bringing termini of the DNA strands together so that they can be joined by ligase. In the presence of PCR reagents and primers that recognize the primer binding sites on the two DNA strands, a region of the ligated sequence may be amplified and detected by real time PCR. In contrast, unligated strands are not amplified and therefore not detected in the assay.

It will be appreciated that the assay also may be used to assay for non-protein molecules that are specifically bound by a nucleic acid aptamer, antibody or other binding agent.

Proximity ligation methods can also be used to detect nucleic acid targets. In this approach, nucleotide sequences complementary to the target are used rather than protein binding agents.

4. Quantitative Real Time PCR and Other Detection and Quantitation Methods.

Any method of detection and/or quantitation of nucleic acids can be used in the invention to detect a probe (PCR, SYBR Green, etc.). In one aspect PCR (polymerase chain reaction) is used to amplify a target. In other aspects, other amplification systems or detection systems are used, including systems described in U.S. Pat. No. 7,118,910, which is incorporated herein by reference. In other aspects, a detection system other than PCR is used (e.g., Invader assays; PE BioSystems). In one aspect, real time quantitation methods are used. For example, a variety of so-called "real time amplification" methods or "real time quantitative PCR" methods can be used to determine the quantity of a target nucleic acid present in a sample by measuring the amount of amplification product formed during or after the amplification process itself. Fluorogenic nuclease assays are one specific example of a real time quantitation method which can be used successfully with the devices described herein. This method of monitoring the formation of amplification product involves the continuous measurement of PCR product accumulation using a dual-labeled fluorogenic oligonucleotide probe (e.g., the "tag-specific probe")—an approach frequently referred to in the literature as the "TaqMan®" method. See U.S. Pat. No. 5,723,591; Heid et al., 1996, Real time quantitative PCR *Genome Res.* 6:986-94, each incorporated herein by reference. It will be appreciated that while this disclosure often refers to "TaqMan® probes" for simplicity, the invention is not limited to use of these probes; any tag-specific probe can be used. In particular any detection method in which the tag-specific probe is a dual-labeled fluorogenic oligonucleotide probe may be used.

5. Sample Preparation, Reagents, Related Equipment, and Molecular Biology Methods Preparations of nucleic acids and polypeptides ("samples") can be obtained from biological sources and prepared using conventional methods known in the art. PCR methods (including rt PCT) and reagents are well known by those of skill in the art and widely described in the literature. Devices for thermocycling and detection of fluorescent or other signals are also known. For illustration and without limiting the invention, examples of biological sources include samples from humans and animals (blood fractions, urine, tissue, cell extracts), plants, environmental sources (e.g., pond water) and the like.

6. Analytical Method of the Invention

It will be appreciated that preferably at least 10, more often at least 25, still more often at least 50, even more often at least 100, in some cases at least 500 and sometimes at least 1000 targets are detected. Thus, the method may make use of at least 10, more often at least 25, still more often at least 50, even more often at least 100, in some cases at least 500 and sometimes at least 1000 target-specific probes. The probes may differ in the terminal sequences specific for the target sequence, or ligands specific for an epitope, as well as at the tag sequence and/or at the primer sequences used to amplify or detect the tag.

The present invention provides new methods for detection and quantification of nucleic acids or proteins ("targets") in one or more samples. The methods provide:

The high specificity of the padlock probe and proximity ligation systems.

The high specificity of PCR.

Rapid screening of >1000 nucleic acid or protein targets through multiplexing.

Accurate quantitation by real-time PCR with a dynamic range at least 3-5 orders of magnitude greater than array-based methods.

The methods can be carried out using microfluidic devices of various configurations. For simplicity, the illustrative examples below describe interrogation of 2304 targets using a Dynamic Array microfluidic device with a 48×48 array of reaction chambers. It will be understood that other configurations are possible and contemplated such as, for example, 48×96; 96×96; 30×120; etc.

For illustration, in the case of nucleic acid detection, the targets can be, for example, nucleic acids associated with pathogens, RNAs for which over- or under-expression is indicative of disease, genomic DNA, or other nucleic acids. For illustration, in the case of protein detection, targets can be polypeptides associated with pathogens, disease states, cell expression states and the like.

The assay usually has a dynamic range of at least 3 orders of magnitude, more often at least 4, even more often at least 5, even more often at least 6, often at least 7, and sometimes at least 8 orders of magnitude.

Terminology

A Dynamic Array microfluidic device with a 48×48 matrix of reaction chambers can be thought of as having 48 columns designated #1-48 in which sample is introduced and 48 rows designated #1-48 in which reagents are introduced. Positions in the array can be described by a coordinate system in which a column and row are specified. Thus [1,1] (column 1, row 1), [1,48], [48,1] and [48,48] would define the four "corners" of the matrix. It will be understood that, as used in this context, for illustration and not limitation, "columns" are microfluidic channels through which sample nucleic acids or proteins are distributed to sample chambers, and "rows" are microfluidic channels through which reagents are distributed to reagent chambers.

A "target-specific probe" means a padlock probe or a proximity probe.

A "tag detecting probe" means a probe, such as a TaqMan® probe, that detects and optionally quantifies a tag sequence.

"Querying" each aliquot of the sample for the presence of a target-specific probe means determining whether a target-specific probe is associated with (e.g., bound to or catenated with) the target, and optionally quantifying the amount of target-specific probe in the sample.

Illustrative Example 1

Analysis of Nucleic Acids from Several Samples (Specific Tags)

In this example, 48 targets are assayed in each of 48 different samples.

The 48 targets to be assayed are referred to as Targets #1-48. For each target a padlock oligonucleotide probe is designed having termini specific to the target (referred to by number), universal PCR primer sites, and one of 48 tag sequences. Thus, for target #4, the padlock oligonucleotide probe is padlock probe #4 and the tag sequence is one of tags #1-48.

For illustration, the assay may be carried out as follows:
1) Process each sample by
   a) adding the 48 padlock oligonucleotide probes;
   b) ligating those oligonucleotides that hybridize to a target molecule, thereby producing circular catenated probes; and
   c) adding exonuclease to remove any unhybridized probes.

In the resulting processed sample, from 0 (if none of the targets is present in the sample) to 48 (if all of the targets are present in the sample) versions of circularized padlock oligonucleotide probes are present, each characterized by a different tag.

2) Load Sample 1 into the column 1 sample channel and distribute to 48 sample chambers. Load Samples 2-48 into columns 2-48, respectively, and distribute each sample to 48 sample chambers. A total of 2304 chambers are loaded.

3) Via the Row 1 reagent channel, distribute universal primers, PCR reagents and a TaqMan® probe that recognizes Tag #1 to the reagent chambers in row 1. Via the Row 2-48 reagent channels, distribute universal primers, PCR reagents and TaqMan® probes that recognize Tags #2-48, respectively, to the corresponding rows.

4) Carry out real-time PCR and monitor.

5) Analysis:

Readout for [1, 1] is for target 1 in Sample 1.
Readout for [1, 2] is for target 2 in Sample 1.
Readout for [2, 3] is for target 3 in Sample 2.
Etc.

Figure 2A:
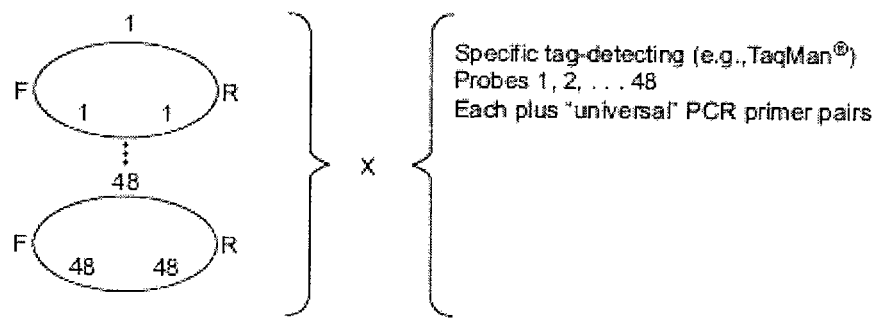
In FIG. 2A selectivity is based on use of multiple tags, as described in Example 1. Each PLP product has a different tag and binds to a different target sequence, and all tags can be amplified using the same forward and reverse primers recognizing the same forward (F) and reverse (R) priming sites. "}x{" indicates that in each aliquot of sample tags are amplified using universal primers and the resulting amplified tags are detected with a tag-specific TaqMan® probe (or other tag-specific tag detecting probe).

Also see FIG. 2A.

Illustrative Example 2

Analysis of Nucleic Acids in One Sample (Specific Tags)

In this example, 2304 targets are assayed in a single sample.

The targets to be assayed are referred to as Targets #1-2304. For each target a padlock oligonucleotide probe (2304 probes total) is designed having (i) termini specific to the target, (ii) universal PCR primer sites, and (iii) one of 48 tag sequences. Thus, for target #4 the padlock oligonucleotide probe is padlock probe #4 and the tag sequence is one of tags #1-48. More specifically,

| Target | Padlock probe # | Tag sequence |
|---|---|---|
| 1-48 | 1-48 | 1-48, respectively |
| 49-96 | 49-96 | 1-48, respectively |
| 97-146 | 97-146 | 1-48, respectively |
| ... | ... | ... |
| 2255-2304 | 2255-2304 | 1-48, respectively |

The assay is carried out as follows:
1) Divide the sample into 48 aliquots.
2) Process each aliquot by
   a) adding 48 padlock oligonucleotide probes to each aliquot (probes 1-48 to Sample 1, probes 49-96 to Sample 2, probes 97-146 to Sample 3, etc.);
   b) ligating those oligonucleotides that hybridize to a target molecule thereby circularizing them; and
   c) adding exonuclease to remove any unhybridized probes.

In the resulting processed aliquots (combined), from 0 (if none of the targets is present in the sample) to 2304 (if all of the targets are present in the sample) versions of circularized padlock oligonucleotide probes are present, each characterized by one of tags 1-48.

3) Load aliquot 1 into column 1, and aliquots 2-48 into columns 2-48, respectively, and distribute to 2304 sample chambers.
4) Via the Row 1 reagent channel, distribute universal primers, PCR reagents and a TaqMan® probe that recognizes Tag #1 to the reagent chambers in row 1. Via the Row 2-48 reagent channels, distribute universal primers, PCR reagents and a TaqMan® probe that recognizes Tags #2-48, respectively.
5) Carry out real-time PCR and monitor.
6) Analysis
Readout for [1, 1] is for target 1.
Readout for [1, 2] is for target 2.
Readout for [2, 3] is for target 51.
Readout for [48, 48] is for target 2304.
Etc.

Illustrative Example 3

Analysis of Proteins

This example describes an assay of each of 48 proteins in 48 different samples.

The 48 proteins to be assayed are referred to as Proteins #1-48. For each protein a pair of monoclonal antibodies that binds the protein, at different epitopes, is obtained. They are referred to as antibody pairs #1-48. Each antibody is attached to a synthetic DNA strand. Each antibody pair has a unique set of two stands such that each pair of strands is recognized by a unique selector oligonucleotide (selector oligonucleotides #1-48). Moreover, the DNA strand sequences are selected so that when any two strands are joined, the resulting sequence includes one of predetermined tag sequences (Tags #1-48) flanked by two PCR universal primer binding sites. Prior to ligation, each synthetic DNA strand has only one of the two PCR binding sites necessary for PCR amplification (i.e., PCR amplification is possible only from the ligated molecules).

The assay is carried out as follows:
1) Process each sample by
   a) adding antibody pairs #1-48;
   b) adding selector oligonucleotides #1-48;
   c) ligating those DNA strands that are joined by the selector oligonucleotide, based on the proximity of the antibodies to which the DNA strands are attached;
In the resulting processed sample, from 0 (if none of the targets is present in the sample) to 48 (if all of the targets are present in the sample) versions of ligated DNAs will be present, each characterized by a different tag.
2) Load Sample 1 into the column 1 sample channel and distribute to 48 sample chambers. Load Samples 2-48 into columns 2-48, respectively, and distribute each sample to 48 sample chambers. A total of 2304 chambers are loaded.
3) Via the Row 1 reagent channel, distribute universal primers, PCR reagents and a TaqMan® probe that recognizes Tag #1 to the reagent chambers in row 1. Via the Row 2-48 reagent channels, distribute universal primers, PCR reagents and TaqMan® probes that recognizes Tags #2-48, respectively to the corresponding rows.
4) Carry out real-time PCR and monitor.

5) Analysis:
Readout for [1, 1] is for target 1 in Sample 1.
Readout for [1, 2] is for target 2 in Sample 1.
Readout for [2, 3] is for target 3 in Sample 2.
Etc.

In Examples 1-3, the PCR amplification step uses universal PCR primers with corresponding universal PCR primer sites on the padlock or proximity probes. Specificity in these methods is due in part to the specificity of the padlock/proximity probe to the target and the specificity of the TaqMan® probes for specific padlock/proximity sequences. In an alternative embodiment, a "universal" TaqMan® probe is used, but the PCR primer sites on the padlock/proximity probes vary. In these embodiments, specificity is due in part to the specificity of the padlock/proximity probe to the target and the specificity of the PCR primers to specific padlock/proximity sequences. In certain applications this approach has advantages. For example, there may be considerable cost savings in using one TaqMan®-type probe, rather than many. In addition in the method of Example 1, supra, the universal PCR primers in any reaction chamber may amplify several different amplicons (if multiple target sequences are present in the chamber). This may reduce specificity, especially in cases in which one target is present in excess over the target corresponding to the specific TaqMan® probe introduced into the chamber.

Although introducing specificity using specific PCR primers and specific TaqMan® probes (as well as the specificity of the padlock/proximity probe for the target) has been described herein, it will be understood by those of skill that intermediate and additive combinations of these approaches may also be used.

Illustrative Example 4

Analysis of Nucleic Acids in 48 Samples (Specific PCR Primers)

Figure 2B:
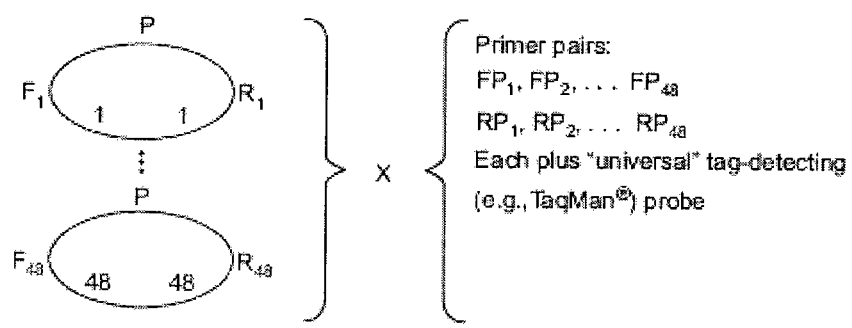
In FIG. 2B selectivity is based on the use of specific primer pairs, as described in Example 4. Each PLP product has the same tag sequence (T) but different primer binding sites, so that the tags for each product are amplified using different primer pairs (e.g., $FP_1+RP_1$), where each primer pair recognizes a unique combination of forward (F) and reverse (R) priming sites, and each amplified tag can be detected using the same ("universal") TaqMan® probe (or other tag detecting probe). Analogous processes may be carried out using proximity probes to detect proteins.

This Example 4 is analogous to Example 1, in that 48 samples are assayed. Also see FIG. 2B. In this example, 48 targets are assayed in each of 48 different samples.

The 48 targets to be assayed are referred to as Targets #1-48. For each target a padlock oligonucleotide probe is designed having termini specific to the target (referred to by number), a universal tag sequence, and one of 48 pairs of PCR primer binding sequences flanking the tag (bound by one of Primer Pairs #1-48). The assay is carried out as follows:
1) Process each sample by
   a) adding the 48 padlock oligonucleotide probes;
   b) ligating those oligonucleotides that hybridize to a target molecule, thereby producing circular catenated probes; and
   c) adding exonuclease to remove any unhybridized probes.
In the resulting processed sample, from 0 (if none of the targets is present in the sample) to 48 (if all of the targets are present in the sample) versions of circularized padlock oligonucleotide probes are present, each characterized by a different tag.
2) Load Sample 1 into the column 1 sample channel and distribute to 48 sample chambers. Load Samples 2-48 into columns 2-48, respectively, and distribute each sample to 48 sample chambers. A total of 2304 chambers are loaded.
3) Via the Row 1 reagent channel, distribute the universal TaqMan® probe, PCR reagents and one PCR primer pair. The primer pair that recognizes padlock probe #1 is added to the reagent chambers in row 1. Via the Row 2-48 reagent channels, distribute primer pairs that recognize padlock probes #2-48, are added.
4) Carry out real-time PCR and monitor.
5) Analysis:
Readout for [1, 1] is for target 1 in Sample 1.
Readout for [1, 2] is for target 2 in Sample 1.
Readout for [2, 3] is for target 3 in Sample 2.
Etc.

Illustrative Example 5

Analysis of Nucleic Acids in One Sample (Specific PCR Primers)

In this example, 2304 targets are assayed in a single sample. Also see FIG. 3.

The targets to be assayed are referred to as Targets #1-2304. For each target a padlock oligonucleotide probe (2304 probes total) is designed having (i) termini specific to the target, (ii) a universal tag sequence and (iii) a unique PCR primer site pair (referred to as forward primers $F_N$ and reverse primers $R_N$, where N is 1 to 48). Thus, for target #4 the padlock oligonucleotide probe is padlock probe #4, and the PCR primer pair is defined by one of forward primers #1-48 and one of reverse primers #1-48.

The assay is carried out as follows:
1) The padlock (or in alternative embodiments, proximity) assay is carried out using 2304 padlock probes;
2) The Sample is divided into 48 aliquots and forward primers are added as follows:

| Target | Padlock probe # | Forward Primer sequence |
|---|---|---|
| 1-48 | 1-48 | 1-48, respectively |
| 49-96 | 49-96 | 1-48, respectively |
| 97-146 | 97-146 | 1-48, respectively |
| ... | ... | ... |
| 2255-2304 | 2255-2304 | 1-48, respectively |

3) Load aliquot 1 into column 1, and aliquots 2-48 into columns 2-48, respectively, and distribute to 2304 sample chambers.
4) Via the Row 1 reagent channel, distribute PCR reagents, the universal TaqMan® probe, and the reverse primer (e.g., $R_1$) corresponding to Target 1. Via the Row 2-48 reagent channels, distribute PCR reagents, the universal TaqMan® probe, and one of the reverse primers 2-48 (e.g., $R_{2-48}$), respectively.
5) Carry out real-time PCR and monitor.
6) Analysis
Readout for [1, 1] is for target 1.
Readout for [1, 2] is for target 2.
Readout for [2, 3] is for target 51.
Readout for [48, 48] is for target 2305.
Etc.

It will be appreciated by one guided by this disclosure that that numerous variations of methods described in these examples may be carried out, and that the examples above are for illustration and not intended to limit the invention in any fashion. It will further be appreciated that, although the examples above describe a device with a 48×48 matrix of reaction chambers and analysis of one or 48 samples are analyzed, many other combinations are possible. For example, many other matrices may be used (as described above) and intermediate numbers of samples may be analyzed. For example, in a 48×48 matrix the number of samples may be any divisor of 48 that gives a whole integer product. More generally, a C×R array can be used to assay the number n samples for CR/n targets, where C/n is a whole integer.

Example 6

Dynamic Array Device

As noted above, one example of a dynamic array device that can be used to practice the methods of the invention is the "48.48 Dynamic Array" (Fluidigm Corp., S. San Francisco Calif.). FIG. 1 depicts the 48.48 Dynamic Array with an integrated input frame.

The 48.48 Dynamic Array provides experiment throughput six-fold higher than a 384-microwell plate, while delivering quantitative data on a par with real-time qPCR standards. This nanofluidic chip for TaqMan® assays also provides substantial reductions in time and running costs to complete large-scale gene-expression studies. With the 48.48 chip, laboratories realize the following advantages:

Flexibility to assay any 48 samples against any 48 genes.
Throughput of 2,304 data points per run equivalent to all pair-wise combinations (48×48) of samples and assays loaded into a chip.
Parallel multiplexing of 48 genes per sample.
Only ninety-six liquid-transfer steps for setup.
Reaction volumes of less than ten nanoliters.
Reliable single-copy qPCR detection within reaction chambers.

Higher Throughput, Streamlined Operations

The 48.48 Dynamic Array provides throughput far beyond what is possible with other technologies, yet reduces complexity. The chip's input frame has a footprint and spacing of fluid microwells that are SBS-compliant. For this reason, standard equipment may be used to handle the transfer of samples and TaqMan® assays. The chip's heat spreader, a flat silicon layer bonded to the underside of each chip, ensures good thermal contact necessary for uniform and accurate temperatures among all the PCR reactions. In addition to dynamic arrays, Fluidigm provides hardware and software to automate the entire setup. After assay components have been transferred to the input frame, the NanoFlex™ IFC Controller automatically drives the fluids to respective reaction chambers. The BioMark™ System performs thermal cycling and real-time detection and analysis. Each chip has a unique barcode, which is scanned into the system's computer for ease of tracking.

Efficient Multiplexed Readouts

Dynamic arrays allow unlimited flexibility in experiment setup as well as multiple data points per sample. After any 48 samples and any 48 assays have been transferred to the input frame, the chip's internal network does the work of routing and combining them into 2,304 (48×48) reactions forty-eight readouts for each of 48 samples. Because dynamic arrays precisely partition samples and assays into 10 nanoliter reactions, it is unnecessary to use endogenous controls in each reaction to account for variations in sample volumes. If desired, one or more of the 48 assays may serve as endogenous controls if they are for genes known to be consistently expressed from sample to sample.

Smoother Workflow, Faster Answers

Relative efficiency may also be viewed in light of the density of experiments per run. Managing a gene expression study involving 2,000 samples against a set of 48 genes would require two-hundred-fifty 384-microwell plates as compared to forty-two 48.48 Dynamic Arrays. Completing such a study would take 25 days using microplates compared to four and a half days using dynamic arrays. This increased throughput is achieved with only 96 liquid-transfer steps per chip compared to the 4,608 steps for equivalent throughput on microplates. The radical reduction saves time but also reduces the cost of pipette tips and minimizes errors, sample loss, and freeze-thawing of reaction components associated with microplate-based operations. Taken together, the advantages of dynamic arrays elevate real-time qPCR to an efficient technique for high-throughput gene expression studies.

| Dynamic Array Specifications The 48-48 Dynamic Array for gene expression analysis is a nanofluidic chip for real-time quantification of PCR products. | |
|---|---|
| Components | Specifications |
| Sensitivity | Single copies can be routinely detected if present in the reaction chamber |
| Sample inputs | 48 |
| TaqMan assay inputs | 48 |
| Minimum sample/assay input volume (per frame well) | 5 microliters |
| Reactions per chip | 2,304 |
| Number of liquid transfer steps to load chip | 96 |
| Volume per reaction | 10 nanoliters |
| Sample and TaqMan assay tracking | Unique bancode on each chip |

Although the present invention has been described in detail with reference to specific embodiments, those of skill in the art will recognize that modifications and improvements are within the scope and spirit of the invention, as set forth in the claims which follow. All publications and patent documents (patents, published patent applications, and unpublished patent applications) cited herein are incorporated herein by reference as if each such publication or document was specifically and individually indicated to be incorporated herein by reference. Citation of publications and patent documents is not intended as an admission that any such document is pertinent prior art, nor does it constitute any admission as to the contents or date of the same. The invention having now been described by way of written description and example, those of skill in the art will recognize that the invention can be practiced in a variety of embodiments and that the foregoing description and examples are for purposes of illustration and not limitation of the following claims.

The invention claimed is:

1. An assay method for detection of a plurality of nucleic acid or protein targets in a sample comprising
  (a) combining target-specific probes with the sample under conditions in which at least 25 target-specific probes each bind a different specific target in the sample, if the specific target is present,
  wherein each said target-specific probe comprises a common nucleic acid tag sequence and a unique combination of a first primer binding site and a second primer binding site flanking the nucleic acid tag sequence,
  wherein at least two of said target-specific probes do not have the same first primer binding sites and at least two of said target-specific probes do not have the same second primer binding sites, and
  wherein the target-specific probe forms a target-specific probe product associated with the target if the target is present in the sample, thereby associating the tag with the target by forming a target-specific probe product associated with the target;
  (b) distributing aliquots of the sample to separate compartments of a microfluidic device and segregating the aliquots from each other;
  (c) querying each said aliquot for the presence or absence of a different target-specific probe product, wherein said querying comprises amplifying the nucleic acid tag sequence using a first primer that binds the first primer binding site and a second primer that binds the second primer binding site; and detecting the presence or absence of the common nucleic acid tag sequence using a tag-detecting probe.

2. The method of claim 1 wherein target-specific probes sufficient to identify at least 500 different targets are combined with the sample.

3. The method of claim 1 wherein said querying comprises quantifying the amount of the nucleic acid tag sequence in each aliquot and correlating the amount of the tag sequence with the amount of target in the sample.

4. The method of claim 3 in which the tag sequence is amplified using PCR.

5. The method of claim 4 wherein the amplified tag sequence is detected using a fluorogenic nuclease assay.

6. The method of claim 5 wherein the amplified tag sequence is quantified by the continuous measurement of PCR product accumulation using a dual-labeled fluorogenic oligonucleotide probe.

7. The method of claim 1 wherein the target is a nucleic acid molecule.

8. The method of claim 7 wherein the target-specific probe is a padlock probe.

9. The method of claim 1 wherein the target is a protein molecule.

10. The method of claim 1 wherein the target-specific probe is a proximity probe.

11. The method of claim 1 wherein the assay has a dynamic range of at least 4 orders of magnitude.

12. The method of claim 1 wherein the microfluidic device is fabricated, at least in part, from an elastomeric material.

13. The method of claim 1 wherein querying each aliquot of the sample for the presence of a different target-specific probe comprises combining each aliquot with a composition containing PCR primers and/or a tag detecting probe.

14. The method of claim 13 wherein querying each aliquot of the sample for the presence of a different target-specific probe comprises combining each aliquot with a composition containing PCR primers and a tag detecting probe.

15. The method of claim 14 wherein the tag-detecting probe is a dual-labeled fluorogenic oligonucleotide probe.

16. The method of claim 15 wherein each aliquot is queried using the same tag-detecting probe and a different PCR primer pair.

17. The method of claim 15 wherein each aliquot is queried using the same PCR primer pair and a different tag-detecting probe.

18. An assay method for detection of a plurality of DNA targets in a sample comprising
  combining target-specific padlock probes sufficient to identify at least 25 different targets with the sample under conditions in which the probes bind and cantenate to the target molecules, if present, forming a target-specific probe product
  wherein each probe comprises a common nucleic acid tag sequence and a unique combination of a first primer binding site and a second primer binding site wherein at least two of said target-specific probes do not have the same first primer binding sites and at least two of said target-specific probes do not have the same second primer binding sites, and wherein the padlock probes form target-specific probe products associated with the target if the target is present in the sample, thereby associating the tag sequence with the target distributing aliquots of the sample to separate compartments of a microfluidic device and segregating the aliquots from each other;

querying each aliquot for the presence of a different probe molecule catenated to the target, wherein said querying comprises detecting the tag sequence if present in the aliquot, and wherein detecting the tag comprises amplifying the tag sequence using a first primer that binds the first primer binding site and a second primer that binds the second primer binding site and detecting the amplification using a dual-labeled fluorogenic oligonucleotide probe.

* * * * *